(12) United States Patent
Strzepa et al.

(10) Patent No.: US 8,092,530 B2
(45) Date of Patent: Jan. 10, 2012

(54) CARTILAGE IMPLANTS

(75) Inventors: Peter Strzepa, Austin, TX (US);
Stephen D. Cook, New Orleans, LA (US)

(73) Assignee: MoiRai Orthopedics, LLC, Metairie, LA (US)

( * ) Notice: Subject to any disclaimer, the term of this patent is extended or adjusted under 35 U.S.C. 154(b) by 0 days.

(21) Appl. No.: 12/687,672

(22) Filed: Jan. 14, 2010

(65) Prior Publication Data
US 2010/0121451 A1    May 13, 2010

Related U.S. Application Data

(62) Division of application No. 12/074,770, filed on Mar. 6, 2008, now Pat. No. 8,043,375.

(51) Int. Cl.
*A61F 2/08* (2006.01)
*A61F 2/28* (2006.01)
(52) U.S. Cl. ............... 623/14.12; 623/16.11; 623/18.11
(58) Field of Classification Search ............... 623/14.12, 623/23.44, 16.11, 18.11, 20.18, 23.48, 23.5
See application file for complete search history.

(56) References Cited

U.S. PATENT DOCUMENTS

| | | |
|---|---|---|
| 4,158,894 A | 6/1979 | Worrell |
| 4,231,121 A | 11/1980 | Lewis |
| 4,281,419 A | 8/1981 | Treace |
| 4,849,692 A | 7/1989 | Blood |
| 4,919,667 A | 4/1990 | Richmond |
| 4,945,305 A | 7/1990 | Blood |
| 4,964,867 A | 10/1990 | Boger |
| 5,019,104 A | 5/1991 | Whiteside et al. |
| 5,236,462 A | 8/1993 | Mikhail |
| 5,246,460 A | 9/1993 | Goodfellow et al. |
| 5,263,987 A | 11/1993 | Shah |
| 5,306,311 A | 4/1994 | Stone |
| 5,358,525 A | 10/1994 | Fox |
| 5,580,353 A | 12/1996 | Mendes et al. |

(Continued)

FOREIGN PATENT DOCUMENTS

CA    2232068    3/1997

(Continued)

OTHER PUBLICATIONS

PCT International Search Report Issued in Connection with International Application No. PCT/US2010/046654; Nov. 29, 2010; 1-5 pages.

(Continued)

*Primary Examiner* — David Isabella
*Assistant Examiner* — Marcia Hoffman
(74) *Attorney, Agent, or Firm* — Greenberg Traurig, LLP

(57) ABSTRACT

Cartilage implant devices having oval articular ends are provided. The articular ends have a convex upper face and a concave lower face. The convex upper face has a first circular pitch radius and a first circular roll radius. The concave lower face has a first surface comprising a second circular pitch radius and a second circular roll radius, and at least two second surfaces each second surface having a third circular pitch radius and a third circular roll radius. The convex upper face blends into a rim, wherein at least a first and second portion of the rim extends at least a first distance along the vertical axis and a third and fourth portion of the rim tapers inward along the vertical axis, the rim blends into the concave lower face. The implant devices further have a stem extending from the concave lower face away from the convex upper face.

9 Claims, 3 Drawing Sheets

U.S. PATENT DOCUMENTS

| | | |
|---|---|---|
| 5,600,330 A | 2/1997 | Blood |
| 5,609,640 A | 3/1997 | Johnson |
| 5,645,605 A | 7/1997 | Klawitter |
| 5,742,394 A | 4/1998 | Hansen |
| 5,744,953 A | 4/1998 | Hansen |
| 5,749,874 A | 5/1998 | Schwartz |
| 5,767,669 A | 6/1998 | Hansen et al. |
| 5,767,960 A | 6/1998 | Orman et al. |
| 5,782,835 A | 7/1998 | Hart |
| 5,782,927 A | 7/1998 | Klawitter et al. |
| 5,831,260 A | 11/1998 | Hansen |
| 5,953,683 A | 9/1999 | Hansen et al. |
| 6,159,247 A | 12/2000 | Klawitter et al. |
| 6,172,499 B1 | 1/2001 | Ashe |
| 6,217,616 B1 | 4/2001 | Ogilvie |
| 6,246,231 B1 | 6/2001 | Ashe |
| 6,417,839 B1 | 7/2002 | Odell |
| 6,436,146 B1 | 8/2002 | Hassler et al. |
| 6,473,167 B1 | 10/2002 | Odell |
| 6,528,991 B2 | 3/2003 | Ashe |
| 6,575,986 B2 | 6/2003 | Overaker |
| 6,610,067 B2 | 8/2003 | Tallarida et al. |
| 6,626,945 B2 | 9/2003 | Simon |
| 6,626,950 B2 | 9/2003 | Brown et al. |
| 6,679,917 B2 | 1/2004 | Ek |
| 6,699,292 B2 | 3/2004 | Ogilvie et al. |
| 6,709,460 B2 | 3/2004 | Merchant |
| D490,900 S | 6/2004 | Ogilvie et al. |
| 6,754,596 B2 | 6/2004 | Ashe |
| 6,784,660 B2 | 8/2004 | Ashe |
| 6,797,006 B2 | 9/2004 | Hodorek |
| 6,814,757 B2 | 11/2004 | Kopylov |
| 6,815,651 B2 | 11/2004 | Odell |
| 6,854,972 B1 | 2/2005 | Elian |
| 6,856,823 B2 | 2/2005 | Ashe |
| 7,027,634 B2 | 4/2006 | Odell |
| 7,106,431 B2 | 9/2006 | Odell |
| 7,161,686 B2 | 1/2007 | Duling et al. |
| 7,204,854 B2 | 4/2007 | Guederian et al. |
| 7,264,634 B2 | 9/2007 | Schmieding |
| 7,314,488 B2 | 1/2008 | Reiley |
| 8,012,217 B2 | 9/2011 | Strzepa et al. |
| 2003/0135280 A1 | 7/2003 | Kopylov et al. |
| 2003/0233149 A1 | 12/2003 | Hodorek |
| 2004/0039447 A1 | 2/2004 | Simon et al. |
| 2004/0230303 A1 | 11/2004 | Gomes et al. |
| 2004/0230315 A1 | 11/2004 | Ek |
| 2005/0033426 A1 | 2/2005 | Ogilvie et al. |
| 2005/0084513 A1 | 4/2005 | Tang |
| 2005/0137708 A1 | 6/2005 | Clark |
| 2005/0137713 A1 | 6/2005 | Bertram |
| 2006/0069446 A1 | 3/2006 | Ragusa et al. |
| 2006/0190002 A1 | 8/2006 | Tallarida et al. |
| 2006/0229726 A1 | 10/2006 | Ek |
| 2006/0241778 A1 | 10/2006 | Ogilvie |
| 2007/0032876 A1 | 2/2007 | Clark |
| 2007/0078334 A1 | 4/2007 | Scully et al. |
| 2007/0123993 A1 | 5/2007 | Hassler et al. |
| 2007/0198095 A1 | 8/2007 | VanDer Meulen et al. |
| 2007/0225820 A1 | 9/2007 | Thomas et al. |
| 2007/0250169 A1 | 10/2007 | Lang |
| 2008/0188942 A1 | 8/2008 | Brown et al. |

FOREIGN PATENT DOCUMENTS

| | | |
|---|---|---|
| DE | 69732500 T | 4/2006 |
| DE | 602004003510 T | 8/2007 |
| DE | 60126129 T | 11/2007 |
| EP | 1112753 | 2/2001 |
| EP | 1437104 | 7/2004 |
| EP | 1955676 A1 | 8/2008 |
| ES | 2141533 T | 3/2000 |
| JP | 2004202233 | 7/2004 |
| WO | WO-8802844 | 4/1988 |
| WO | WO-9012276 | 10/1990 |
| WO | WO-9203117 | 3/1992 |
| WO | WO-9602008 | 1/1996 |
| WO | WO-9710780 | 3/1997 |
| WO | WO-9819637 | 5/1998 |
| WO | WO-0013617 | 3/2000 |
| WO | WO-0133162 | 5/2001 |
| WO | WO-0170138 | 9/2001 |
| WO | WO-0243627 | 6/2002 |
| WO | WO-2004093767 | 11/2004 |
| WO | WO-2007041678 | 4/2007 |
| WO | WO-2007059459 | 5/2007 |
| WO | WO-2007019752 | 9/2007 |
| WO | WO-2007103362 | 9/2007 |

OTHER PUBLICATIONS

PCT Written Opinion of the International Searching Authority Issued in Connection with International Application No. PCT/US2010/046654; Nov. 29, 2010; 1-8 pages.

Non-Final Office Action Issued Against U.S. Appl. No. 12/074,770; Nov. 24, 2010; 1-14 pages.

Non-Final Office Action Issued Against U.S. Appl. No. 12/319,869; Nov. 29, 2010; 1-16 pages.

"Pyrocarbon in Orthopedics," downloaded from www.pyrocarbon.com/pyrocarbon-orthopedic-implants.php on Feb. 12, 2008, pp. 1-4.

"Pyrolytic Carbon" downloaded from http://en.wikipedia.org/wiki/Pyrolytic_carbon on Feb. 12, 2008, p. 1-2.

PCT International Search Report for International Application No. PCT/US09/36159.

PCT Written Opinion of the International Searching Authority for International Application No. PCT/US09/36159.

PCT International Search Report for International Application No. PCT/US09/49441.

PCT Written Opinion of the International Searching Authority for International Application No. PCT/US09/49441.

Office Action dated Dec. 28, 2009 issued against U.S. Appl. No. 12/074,770.

Office Action dated Apr. 27, 2010 issued against U.S. Appl. No. 12/074,770.

U.S. Patent and Trademark Office; Notice of Allowance and Fee(s) Due Issued in Connection with U.S. Appl. No. 12/319,869; Jun. 24, 2011; 15 pages; U.S.A.

U.S. Patent and Trademark Office; Non-Final Office Action Issued Against U.S. Appl. No. 12/396,872; Jul. 6, 2011; 28 pages; U.S.A.

CARTILAGE IMPLANTS

CROSS-REFERENCE TO RELATED APPLICATIONS

This is a divisional patent application of U.S. patent application Ser. No. 12/074,770, filed on Mar. 6, 2008 now U.S. Pat. No. 8,043,375.

FIELD OF THE INVENTION

This invention relates to devices and methods for the repair of articular cartilage defects. In particular, this invention relates to new and improved implants that serve as a replacement for diseased cartilage in joints such as human knees, hips and shoulders.

BACKGROUND OF THE INVENTION

Cartilage acts as a pad between bones to reduce friction and prevent the bones from grinding against one another. Cartilage covers the articular surface of many, if not all, joints in the body. The smoothness and thickness of the cartilage are factors that determine the load-bearing characteristics and mobility of the joints. Over time, due to injury or heredity, however, lesions such as fissures, cracks or crazes can form in the cartilage. In some cases, osteochondral, the lesion penetrates to the subchondral surface of the bone. In other cases, chondral, the lesion does not penetrate to the subchondral surface of the bone. In any event, lesions generally do not repair themselves—and if any repair is made it is insufficient to heal—leading to significant pain and disability, either acutely or over time. Thus, there has long been a need to treat, repair, or regenerate damaged articular cartilage.

One approach for regenerating new cartilage is autologous chondrocyte transplantation. However, this technique is complex and relatively costly. Other techniques, aimed at repair instead of regeneration, include debridement, lavage, microfracturing, drilling, and abrasion arthroplasty. These procedures generally involve penetrating the region of vascularization in the subchondral bone with an instrument until bleeding occurs. Formation of a fibrin clot differentiates into fibrocartilage, which then covers the defect site. Some have found, however, that the resulting repair tissue is relatively weak, disorganized, and lacks the biomechanical properties of normal hyaline cartilage that typically covers the bone ends. Additionally, this technique can generally only be used on chondral defects in the presence of normal joint congruity.

An alternative approach has been to undergo a total replacement of the joint. Such total replacements, however, are costly, high risk, and involve a long recovery time. Accordingly, there is a need for alternative treatments.

The above-identified prior art devices and methods, as well as alternative devices and methods, are illustrated in greater detail in the following patents and patent publications:

U.S. Patent Pub. No. 2005/0137708 to Clark discloses, inter alia, a knee joint resurfacing implant that may include femoral implant and tibial implant components. The femoral implant components may be attached to the femur using screws or other fixation devices, and may be configured to share loads between cortical and cancellous bone material. The tibial implant components are formed in modular portions which may be assembled within the knee joint and may be free-floating or fixed to the tibial surface.

U.S. Patent Pub. No. 2007/0032876 to Clark discloses, inter alia, a knee joint prosthesis including femoral and tibial components. The bodies of the components may possess a network of channels which may be used to deliver bone cement to the component bone interface after the components are implanted.

U.S. Patent Pub. No. 2007/0250169 to Lang discloses, inter alia, methods and devices for repairing articular surfaces. The devices of Lang are customizable, or patient specific, implants configured for placement between joint surfaces formed by inserting a hollow device having an aperture and a lumen into a target joint, and injecting material into the hollow device to form an implant.

U.S. Pat. No. 6,679,917 to Ek discloses, inter alia, an implant for installation into a portion of an articular surface including a protrusion configured to cover an un-excised portion of articular surface proximate to the implant.

U.S. Pat. No. 6,814,757 to Kopylov, et al. discloses, inter alia, a joint surface replacement or joint prosthesis for the distal radioulnar joint.

Accordingly, what is needed is a minimally invasive, cost effective, implant, which preserves as much of the normal, natural, cartilage as possible. Also needed is an implant that restores much of the patient's range of motion, maintains that restored motion over a long period of time, and requires a relatively short rehabilitation period.

SUMMARY OF THE INVENTION

Definitions

For the purposes of this disclosure, the terms "vertical axis" or "vertical" mean a direction from the top of a three-dimensional object to the bottom of the three-dimensional object.

For the purposes of this disclosure, the term "yaw" means a direction of rotation around the vertical axis.

For the purposes of this disclosure, the terms "horizontal axis" or "horizontal" mean a direction from right of the three-dimensional object to the left of the three-dimensional object.

For the purposes of this disclosure, the term "pitch" means a direction of rotation around the horizontal axis.

For the purposes of this disclosure, the terms "depth axis" or "depth" mean a direction from the front of the three-dimensional object to the back of the three-dimensional object.

For the purposes of this disclosure, the term "roll" means a direction of rotation around the depth axis.

For the purposes of this disclosure, the term "spherical radius" means the curvature of a surface formed by a sphere having a particular radius. Accordingly, when a surface is referred to as having a spherical radius, it is meant that the surface has a curvature equal to the curvature of the surface of a sphere having a particular radius.

For the purpose of this disclosure, the term "circular yaw radius" means the maximum curvature about yaw of a surface formed by a circle having a particular radius rotated about yaw.

For the purpose of this disclosure, the term "circular roll radius" means the maximum curvature about roll of a surface formed by a circle having a particular radius rotated about roll.

For the purpose of this disclosure, the term "circular pitch radius" means the maximum curvature about pitch of a surface formed by a circle having a particular radius rotated about pitch.

For the purpose of this disclosure, the term "oval" means two semi-circles connected by two straight line segments that do not intersect and that each are tangent to each semi-circle, alternatively the term "oval" means an oblong three-dimensional closed curve having no straight segments.

For the purpose of this disclosure, the term "torus" means the surface of a toriod.

For the purpose of this disclosure, the term "tubular radius" refers to the radius of the tube of a torus, as opposed to the radius from the center of the torus to the center of the tube.

For the purpose of this disclosure, geometric terms such as "oval", "circle", "sphere", "cylinder", and the like are used as references and for clarity of understanding, as would be understood by one of ordinary skill in the art. Accordingly, these terms should not be limited to strict Euclidean standards.

The present invention provides a cartilage implant, preferably for use in human joints, including knees. In accordance with one important aspect of the present invention a cartilage implant is provided which includes an articular end having a circular perimeter, a convex upper face, and a concave lower face. The convex upper face has a spherical radius and the concave lower face has a spherical radius. The implant additionally includes a stem extending from the concave lower face away from the convex upper face along a vertical axis. The stem has a circular perimeter which is a maximum at the intersection of the stem and the concave lower face, and which decreases to a lesser circular perimeter along the vertical axis of the stem. Preferably, the maximum stem circular perimeter is less than the articular end circular perimeter.

In accordance with another important aspect of the present invention, a cartilage implant is provided, which includes an articular end having an oval perimeter, a convex upper face and a concave lower face. The convex upper face of the oval articular end has a first circular pitch radius and a first circular roll radius. The concave lower face of the oval articular end has a first surface comprising a second circular pitch radius and a second circular roll radius, and at least two second surfaces both external to the first surface and each other and both tangent to the first surface and each having a third circular pitch radius and a third circular roll radius. Preferably, the convex upper face blends into a rim, wherein at least first and second portions of the rim extend at least a first distance along the vertical axis and third and fourth portions of the rim taper inward along the vertical axis, and the rim further blends into the concave lower face. The cartilage implant further includes a stem extending from the concave lower face away from the convex upper face. Preferably, the stem has an oval shaped perimeter in a plane perpendicular to the vertical axis.

Those skilled in the art will further appreciate the above-mentioned advantages and superior features of the invention together with other important aspects thereof upon reading the detailed description which follows in conjunction with the drawings, in which like parts are given like reference numerals, and the vertical, horizontal and depth orientations of a given embodiment are specified explicitly in at least one drawing of the embodiment.

BRIEF DESCRIPTION OF THE DRAWINGS

The drawing figures are not necessarily to scale and certain features of the invention may be shown exaggerated in scale or in somewhat schematic form in the interest of clarity and conciseness, wherein.

DISCLOSURE OF ALTERNATIVE EMBODIMENTS

Figure 1:
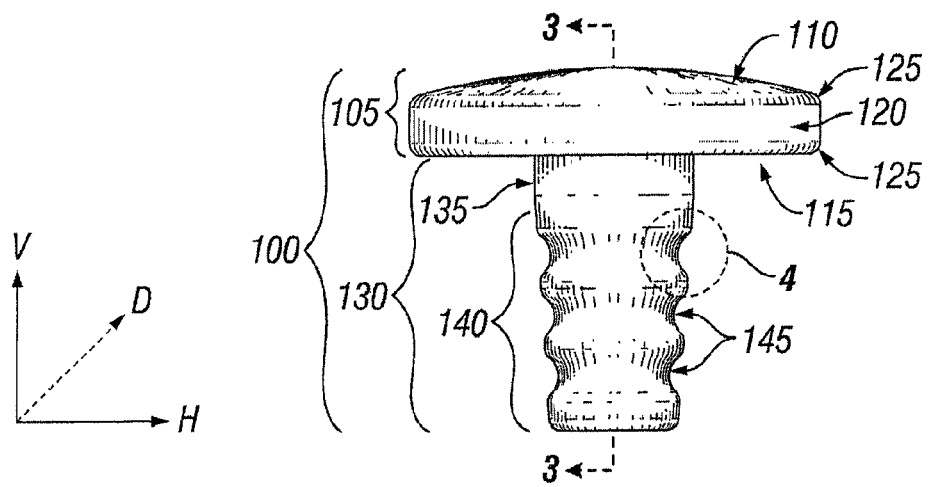
FIG. 1 is a front view of one embodiment of a cartilage implant.

FIG. 1 illustrates one embodiment of a cartilage implant 100, in which the vertical, V, horizontal, H, and depth, D, orientations of this embodiment are depicted. The cartilage implant 100 preferably has an articular end 105 and a stem 130. The articular end 105 may be a disk of uniform thickness in the vertical or a cylinder of uniform length in the vertical. Preferably, the articular end 105 has a convex upper face 110, which blends 125 into, and is bounded by, a circular perimeter portion 120, which—after some length—itself blends 125 into a concave lower face 115.

In this embodiment, the circular pitch radius of the convex upper face 110 is about the same as the circular roll radius of the convex upper face 110. The circular pitch radius and the circular roll radius of the convex upper face 110 may be from about 25 to about 40 millimeters, preferably from about 30 to about 35 millimeters, most preferably about 32 millimeters. The convex upper face 110 preferably blends, as at 125, into the circular perimeter 120, with the blend 125 having an edge radius of from about 0.1 millimeters to about 1 millimeter. Alternatively, the blend may be about 0.5 millimeters.

Figure 2:
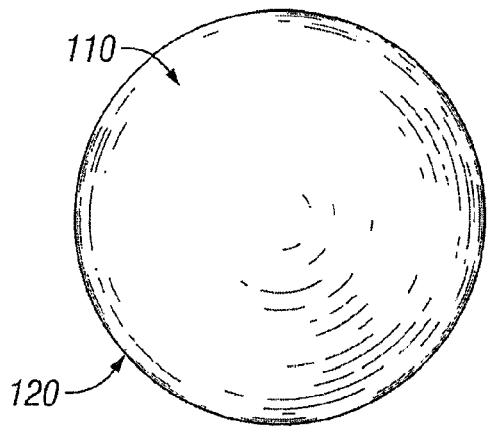
FIG. 2 is a top-down view of the embodiment of FIG. 1.
Figure 3:
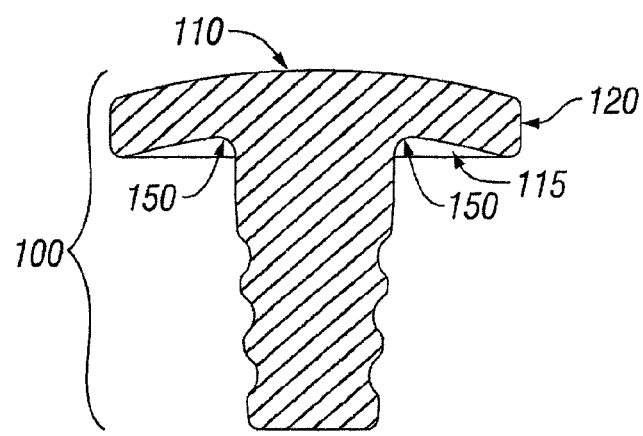
FIG. 3 is a cut-away view of the cartilage implant of FIG. 1 taken along line 3-3.

The circular perimeter 120 may extend some distance along the vertical axis, thereby forming a cylinder between the convex upper face 110 and the concave lower face 115. The length of the cylinder formed by the circular perimeter 120 ranges from about one millimeter to about 5 millimeters, and preferably from about 2 millimeters to about 3 millimeters. Referring to FIG. 2, the diameter of the circular perimeter 120 may be of any length and preferably ranges from about 10 millimeters to about 30 millimeters, alternatively from about 12 millimeters to about 20 millimeters. Most preferred diameters of the circular perimeter 120 include about 12.5 millimeters, about 15 millimeters, about 17.5 millimeters, and about 20 millimeters. Continuing with respect to FIG. 1, in a further embodiment, the circular perimeter 120 may blend 125 into the concave lower face 115. Preferably, the blend 125 is an edge radius of from about 0.1 millimeters to about 1 millimeter, alternatively about 0.5 millimeters.

The circular pitch radius of the concave lower face 115 may be about the same as the circular roll radius of the concave lower face 115. In this embodiment, the circular pitch radius and the circular roll radius of the concave lower face 115 may be of any length and preferably range from about 20 to about 40 millimeters, alternatively from about 25 to about 35 millimeters. A most preferred circular pitch radius and circular roll radius of the concave lower face 115 is about 30 millimeters. Preferably, the circular pitch and roll radii of the convex upper face 110 are greater than the circular pitch and roll radii of the concave lower face 115. In a preferable embodiment, the circular pitch and roll radii of the convex upper face 110 are about concentric with the circular pitch and roll radii of the concave lower face 115.

A stem 130 preferably extends from the concave lower face 115 in the vertical direction away from the convex upper face 110. Preferably, the stem 130 blends 150 into the concave lower face 115. Preferably, the blend 150 is a fillet radius of from about 0.1 millimeters to about 1.5 millimeters, alternatively about 0.8 millimeters. The center of the stem 130 about its yaw is preferably concentric with the center of the circular perimeter 120 about its yaw. The stem 130 preferably has a maximum stem yaw radius at the intersection of the stem 130 and the concave lower face 115. The maximum stem yaw radius is preferably less than the circular perimeter 120 yaw radius. In this embodiment, the stem yaw radius tapers from its maximum to a lesser stem yaw radius along the vertical length of the stem 130. In this embodiment, the stem 130 is generally conical along its entire vertical length. In a still further embodiment, the overall vertical length of the stem 130 is preferably at least 50% of the diameter of the circular perimeter 120.

Alternatively, the stem 130 has a cylindrical portion 135 extending from the concave lower face 115 in the vertical direction away from the concave upper face 110, and a conical portion 140 further extending from the end of the cylindrical portion 135 in the vertical direction away from the concave upper face 110. The cylindrical portion 135 may be of any length and preferably has a length along its vertical axis of from about one millimeter to about 5 millimeters, alternatively from about 2 millimeters to about 3 millimeters. The cylindrical portion 135 may have a circular yaw radius of any length, preferably from about 1 millimeter to about 5 millimeters, alternatively from about 2 millimeters to about 4 millimeters. Most preferred circular yaw radii of the cylindrical portion 135 include about 2.75 millimeters, about 3.125 millimeters, about 3.375 millimeters, and about 3.625 millimeters. Without wishing to be bound by the theory, the cylindrical portion 135 is preferable as it allows for ease of manufacturing, i.e., it provides a physical structure to clamp during manufacturing.

The conical portion 140 may be of any length and preferably ranges along its vertical length from about 2 millimeters to about 15 millimeters, alternatively from about 5 millimeters to about 15 millimeters, and alternatively from about 8.5 millimeters to about 11 millimeters. In this embodiment, the maximum circular yaw radius of the conical portion 140 is located at the intersection between the conical portion 140 and the cylindrical portion 135, and is equal to the circular yaw radius of the cylindrical portion 135. The conical portion 140 preferably has yaw radii that decrease from the maximum to a minimum along its vertical axis in the direction away from the upper convex face 110. The circular yaw radii of the conical portion 140 may be of any length, and preferably ranges from about one millimeter to about 5 millimeters, alternatively from about 2 millimeters to about 3 millimeters.

Figure 4:
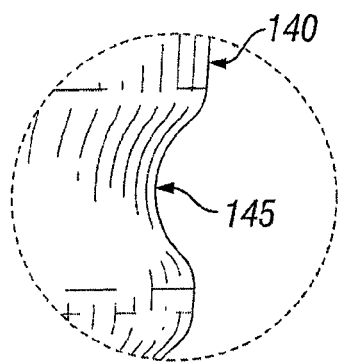
FIG. 4 is an exploded view of a portion of the front view of FIG. 1.

With respect to FIG. 4, the conical portion 140 preferably has circumferential grooves 145 around its perimeter. The shape of the circumferential grooves 145 may be defined by a partial torus having a tubular radius of any length, and preferably ranges from about 0.25 millimeters to about 2 millimeters, more preferably from about 0.5 millimeters to about 1 millimeter, most preferably about 1 millimeter. The circumferential grooves 145 are spaced apart at any distance, and preferably from about 1 to about 3 millimeters from each other along the vertical, more preferably from about 2 to about 2.5 millimeters.

Figure 5:
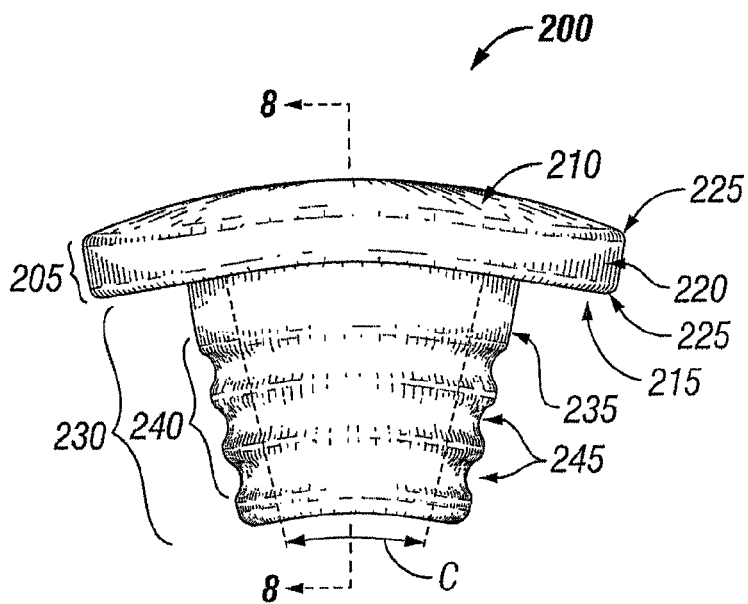
FIG. 5 is a front view of an alternative embodiment of a cartilage implant.
Figure 6:
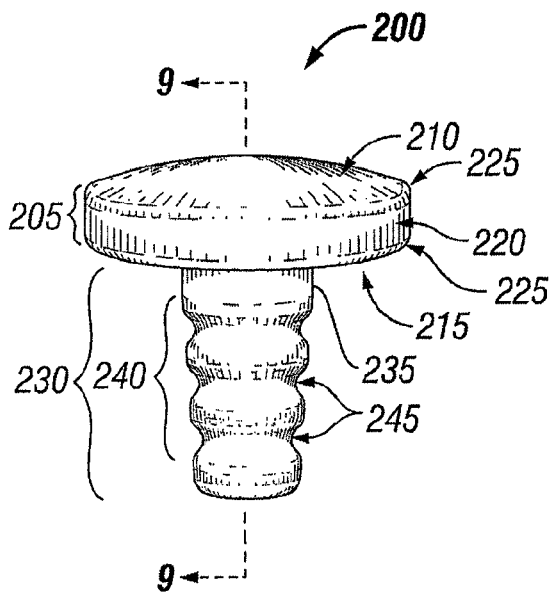
FIG. 6 is a side view of the embodiment of FIG. 5.
Figure 7:
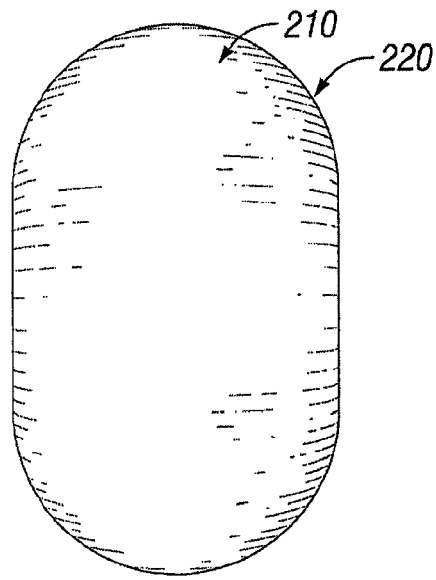
FIG. 7 is a top-down view of the embodiment of FIG. 6.

FIGS. 5 and 6 illustrate an alternative embodiment of a cartilage implant 200. The vertical, V, horizontal, H, and depth, D, orientations of this alternative embodiment of the cartilage implant 200 are depicted in FIG. 5. The cartilage implant 200 preferably has an articular end 205 and a stem 230. The articular end 205 may be an oval column of uniform thickness in the vertical having planar surfaces at its upper and lower faces. Preferably, however, with respect to FIGS. 5, 6, and 7, the articular end 205 has a convex upper face 210, which blends, as at, 225 into, and is bounded by, an oval perimeter 220, which—after some length—itself blends 225 into a concave lower face 215. Preferably, the blends 225 have an edge radius from about 0.1 millimeters to about 1 millimeter. Alternatively the blends 225 may be about 0.5 millimeters.

With respect to FIG. 5, and in an embodiment the maximum length of the articular end 205 along the horizontal axis may be any length and preferably ranges from about 15 millimeters to about 40 millimeters, more preferably from about 20 millimeters to about 35 millimeters. Most preferred maximum lengths of the articular end 205 along the horizontal axis include about 20 millimeters, about 22.5 millimeters, about 25 millimeters, about 27.5 millimeters, and about 30 millimeters. The maximum length of the articular end 205 along the depth axis may be of any length and preferably ranges from about 10 millimeters to about 30 millimeters, alternatively from about 15 millimeters to about 25 millimeters. Most preferred maximum lengths of the articular end 205 along the depth axis include about 15 millimeters, about 17.5 millimeters, and about 20 millimeters. In this embodiment the maximum length of the cartilage implant 200 along the vertical axis may be of any length and preferably ranges from about 10 millimeters to about 35 millimeters, alternatively from about 10 millimeters to about 20 millimeters. In a most preferred embodiment, the maximum length of the cartilage implant 200 along the vertical axis is about 15 millimeters.

With respect to FIG. 5, the circular pitch radius of the convex upper face 210 may be of any length and preferably ranges from about 15 millimeters to about 30 millimeters, alternatively from about 20 millimeters to about 25 millimeters. A most preferred length of the circular pitch radius of the convex upper face 210 is about 22 millimeters. The circular roll radius of the convex upper face 210 may be of any length and preferably ranges from about 20 millimeters to about 40 millimeters, alternatively from about 25 millimeters to about 35 millimeters. A most preferred length of the circular roll radius of the convex upper face 210 is about 32 millimeters. The convex upper face 210 has a circular pitch radius and a circular roll radius, which are preferably different values.

In an embodiment the concave lower face 215 has one region of curvature, and in a preferable embodiment the concave lower face 215 has at least three distinct regions of curvature. Preferably a first region of curvature is approximately bounded by the lines shown in FIG. 5 forming angle C. Angle C may be any amount of degrees, and preferably ranges from about 5 degrees to about 25 degrees, alternatively from about 10 degrees to about 20 degrees. In this first region of curvature there is a second circular pitch radius and a second circular roll radius, which may have the same or different values, preferably ranging from about 15 millimeters to about 40 millimeters, alternatively from about 20 millimeters to about 25 millimeters. Most preferred values for the second circular pitch radius include about 19.5 millimeters and for the second circular roll radius include about 29.5 millimeters. In the second and third regions of curvature, which occupy that portion of the concave lower face 215 not occupied by the first region, there is a third circular pitch radius and a third circular roll radius, which may have the same or different values preferably ranging from about 15 millimeters to about 40 millimeters, alternatively from about 20 millimeters to about 25 millimeters. A most preferred value of the third circular pitch radius and the third circular roll radius is about 19.5 millimeters.

Figure 8:
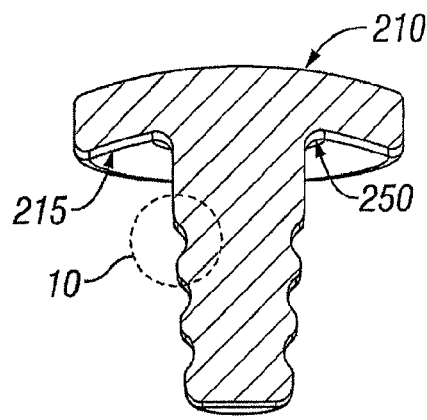
FIG. 8 is a cut-away view of the cartilage implant of FIG. 5 taken along line 8-8.
Figure 9:
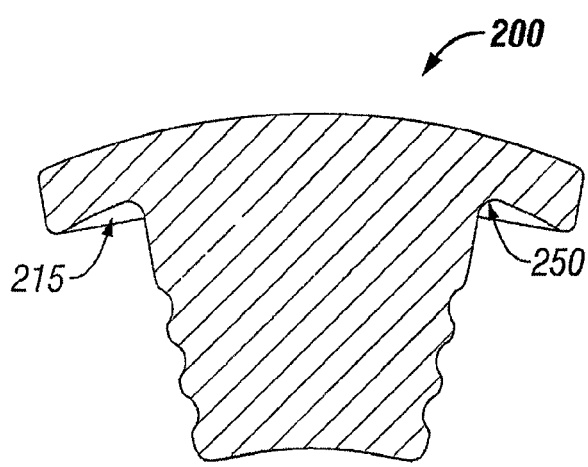
FIG. 9 is a cut-away view of the cartilage implant of FIG. 6 taken along line 9-9.

The stem 230 has two portions, which are both generally oval in cross-section in planes perpendicular to the vertical axis. Preferably, the first portion 235 extends from the concave lower face 215 a length along the vertical in a direction away from the convex upper face 210, and the second portion 240 extends from the end of the first portion 235 a length along the vertical in a direction away from the convex upper face 210. The stem 230 blends 250 into the concave lower face 215 of the articular end 205. Preferably, the blend 250 is a fillet radius of from about 0.1 millimeters to about 1.5 millimeters, most preferably about 0.8 millimeters. The first portion 235 is of a uniform length along the depth and of a decreasing length along the horizontal as it extends in the vertical. The first portion 235 may be of any length along the depth and preferably ranges from about 2 millimeters to about 25 millimeters, alternatively from about 5 millimeters to about 20 millimeters, alternatively from about 5 millimeters to about 10 millimeters. A most preferred length along the depth of the first portion 235 is about 6 millimeters. The length along the horizontal of the first portion 235 decreases from a maximum length at the intersection with the concave lower face 215 to a lesser length as it extends along the vertical. The maximum length of the first portion 235 along the horizontal may be of any length, and preferably ranges from about 5 millimeters to about 20 millimeters, alternatively from about 10 millimeters to about 15 millimeters. With respect to FIG. 8, the first portion 235 may be of any length in the vertical direction, and preferably ranges from about 2 millimeters to about 10 millimeters, alternatively from about 2 millimeters to about 8 millimeters; a most preferred length of the first portion 235 in the vertical direction is about 3.6 millimeters. Without wishing to be bound by the theory, the first portion 235 is preferable as it allows for ease of manufacturing, i.e., it provides a physical structure to clamp during manufacturing.

The second portion 240 preferably decreases from a maximum horizontal length to lesser horizontal length as it extends in the vertical direction. The maximum horizontal length of the second portion 240 is preferably the same as the horizontal length of the first portion 235 at the intersection of the first 235 and second 240 portions. The second portion preferably decreases from a maximum length along the depth to lesser length along the depth as it extends in the vertical direction. The maximum length along the depth of the second portion 240 is preferably the same as the length along the depth of the first portion 235 at the intersection of the first 235 and second 240 portions, and thus preferably ranges in value as recited above with respect to the depth length of the first portion 235. With respect to FIG. 8, the second portion 240 may be of any length along the vertical direction, and preferably ranges from about 2 millimeters to about 25 millimeters, alternatively from about 5 millimeters to about 20 millimeters, alternatively from about 5 millimeters to about 10 millimeters; a most preferred length of the second portion 240 along the vertical direction is about 9.1 millimeters.

Figure 10:
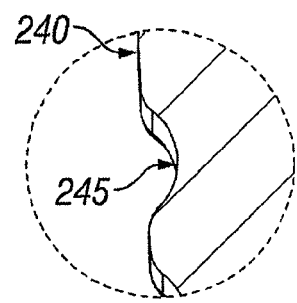
FIG. 10 is an exploded view of a portion of the cut-away view of FIG. 8.

As shown in FIG. 10, the second portion 240 may have grooves 245 about its perimeter. The shape of the grooves 245 may be defined by a partial, oval, non-planar torus having a tubular radius of any length, preferably from about 0.25 millimeters to about 2 millimeters, alternatively from about 0.5 millimeters to about 1 millimeter. Most preferably, the tubular radius of the partial, oval, non-planar torus of the grooves 245 is about 1 millimeter. Preferably the grooves 245 are spaced apart at any distance, and preferably from about 1 to about 3 millimeters from each other along the vertical, more preferably from about 2 to about 2.5 millimeters.

The cartilage implant 100 or 200 many be manufactured from a variety of suitable materials, including any of the following, individually or in combination, graphite, pyrocarbon, ceramic, aluminum oxide, or zirconium oxide; metal and metal alloys, e.g., CO—CR—W—Ni, Co—Cr—Mo, CoCr alloys, CoCr molybdenum alloys, Cr—Ni—Mn alloys; powder metal alloys, 316L or other stainless steels, Ti and Ti alloys including Ti 6Al-4V ELI; polymers, e.g., polyurethane, polyethylene, polypropylene, thermoplastic elastomers; biomaterials such as polycaprolactone; and diffusion hardened materials such as Ti-13-13, zirconium and niobium. Moreover, the cartilage implant 100 or 200 may be coated with a variety of suitable materials, including any of the following, individually or in combination, porous coating systems on bone-contacting surfaces, hydrophilic coatings on load-bearing surfaces, hydroxyapaite coatings on bone-contacting surfaces, and tri-calcium phosphate on bone-contacting surfaces. Other suitable coatings include growth factors and other biological agents such as bone morphogenetic proteins (BMP's), transforming growth factor beta, among others. Additionally, components of the invention may be molded or cast, hand-fabricated or machined.

In this embodiment, the cartilage implant 100 or 200 is composed of graphite and pyrocarbon. Preferably, the cartilage implant 100 or 200 is graphite and includes a coating of pyrocarbon. The pyrocarbon coating may have an average thickness of from about 100 to about 1000 microns, alternatively from about 200 microns to about 500 microns, alternatively from about 250 to about 500 microns, alternatively about 350 microns. The pyrocarbon coating may have an elastic modulus from about 15 gigapascals ("GPa") to about 22 GPa, alternatively about 20 GPa. The pyrocarbon coating may further have a strength of at least 200 megapascals ("MPa"), alternatively at least about 300 MPa, alternatively at least about 400 MPa. The pyrocarbon elastic modulus and strength are preferably tested using four-point bend, third-point-loading substrated specimens of dimensions 25 millimeters by 6 millimeters by 0.4 millimeters. Preferably the pyrocarbon is pyrolytic carbon as described in *Pure Pyrolytic Carbon: Preparation and Properties of a New Material, On-X Carbon for Mechanical Heart Valve Prostheses*, Ely et al, J. Heart Valve Dis., Vol. 7, No. 6, A00534 (November 1998), alternatively pyrocarbon is pyrolytic carbon as described in the before-mentioned J. Heart Valve Dis. publication, but includes additional silicon.

The above-described cartilage implants may be used to repair damaged articular cartilage in humans, including knees, wrists, elbows, shoulders, and the like joints. In a preferred method, a patient having articular cartilage damage is identified. The patient is fully informed of the risks associated of surgery, and consents to the same. An incision is made near the damaged articular cartilage. The lesion to be repaired is identified, and a cartilage implant having dimensions compatible with the lesion is selected. The implant may be slightly smaller or slightly larger than the lesion. In these embodiments, the implant is from about 0.1 percent to about 20 percent smaller or larger than the lesion. A hole is then formed, i.e., drilled, punched, or broached, through the cartilage and the subchondral bone into the cancellous bone. Preferably, the dimensions of the hole are slightly less than the horizontal and depth dimensions of the stem of the implant. This may be achieved, for example, by using a tapered dill bit. Preferably the minimum length of the hole is equal to or slightly greater than the length of the stem of the implant, along the vertical. An amount of healthy and damaged cartilage may be removed near the lesion so that the lower portion of the implant's articular end may rest against the patient's bone. In this manner, however, it is preferable to remove as little healthy cartilage as possible. The stem of the cartilage implant may be inserted into the hole, and the lower portion of the implant's articular end may rest against the bone. The incision is then sutured by any of several known methods.

While specific alternatives to steps of the invention have been described herein, additional alternatives not specifically disclosed but known in the art are intended to fall within the scope of the invention. Thus, it is understood that other applications of the present invention will be apparent to those skilled in the art upon reading the described embodiment and after consideration of the appended claims and drawings.

The invention claimed is:

1. A cartilage implant comprising:
an articular end for repair of articular cartilage defects having an oval perimeter, a convex upper face, and a concave lower face, the convex upper face having a first circular pitch radius and a first circular roll radius, the concave lower face having a first surface comprising a second circular pitch radius and a second circular roll radius, and at least two second surfaces both external to the first surface and both tangent to the first surface, each second surface having a third circular pitch radius and a third circular roll radius, the convex upper face blending into a rim, wherein at least a first and second portion of the rim extends at least a first distance along the vertical axis and a third and fourth portion of the rim tapers inward along the vertical axis, the rim blending into the concave lower face; and
a stem extending from the concave lower face away from the convex upper face, the stem having a plurality of oval shaped perimeters in planes perpendicular to the vertical axis, wherein:
the stem has a first stem portion having a maximum oval shaped perimeter extending at least one millimeter from the concave lower face away from the convex upper face along the vertical axis, and a second stem portion extending from the first stem portion away from the convex upper face along the vertical axis, the second stem portion having a plurality of second stem oval shaped perimeters decreasing in diameter along at least one axis from the maximum oval shaped perimeter of the first portion to a lesser second stem oval shaped perimeter along the vertical axis of the stem; and
wherein the stem has a plurality of circumferential grooves, wherein each circumferential groove extends continuously around at least one of the plurality of second stem oval shaped perimeters, wherein at least one circumferential groove is defined between two adjacent second stem oval shaped perimeters and has a shape of a partial, oval, non-planar torus extending radially inward of the adjacent second stem oval shaped perimeters, wherein the at least one circumferential groove blends into at least one of the two adjacent second stem oval shaped perimeters,
wherein the stem blends into the concave lower face, and wherein the articular end and the stem each consist essentially of: a graphite core and a pyrocarbon coating.

2. The cartilage implant of claim 1, wherein the oval articular end has a maximum length, along the horizontal axis of from about 15 millimeters to about 40 millimeters; the oval articular end has a maximum length, along the depth axis, ranging from about 10 millimeters to about 30 millimeters; and the cartilage implant has a maximum length along the vertical axis ranging from about 10 millimeters to about 35 millimeters.

3. The cartilage implant of claim 1, wherein the first, second and third circular pitch radii are each independently selected from the group consisting of from about 15 millimeters to about 30 millimeters, from about 20 millimeters to about 25 millimeters, about 22 millimeters, and about 19.5 millimeters, the first, second, and third circular roll radii are each independently selected from the group consisting of from about 20 millimeters to about 40 millimeters, from about 25 millimeters to about 35 millimeters, about 32 millimeters, about 29.5 millimeters, and about 19.5 millimeters.

4. The cartilage implant of claim 3, wherein the maximum roll radius of the first surface of the concave lower face is bounded by an angle selected from the group consisting of from about 5 degrees to about 25 degrees and from about 10 degrees to about 20 degrees.

5. The cartilage implant of claim 1, wherein the first stem portion tapers inward along its horizontal axis in the vertical direction and has a uniform length along its depth axis in the vertical direction, the second stem portion tapers inward along its horizontal axis and its depth axis in the vertical direction, the first and second stem portions blend into each other, the length of the first stem portion along the vertical is selected from the group consisting of 2 millimeters to about 10 millimeters and from about 2 millimeters to about 8 millimeters, the length of the second stem portion along the vertical is selected from the group consisting of from about 2 millimeters to about 25 millimeters, from about 5 millimeters to about 20 millimeters, and from about 5 millimeters to about 10 millimeters.

6. The cartilage implant of claim 1, wherein the partial, oval, non-planar torus of the grooves each has a tubular radius of from about 0.25 millimeters to about 1.5 millimeters, and the grooves are spaced apart at a distance of from about 1 millimeter to about 3 millimeters from each other.

7. The cartilage implant of claim 1, wherein the pyrocarbon coating has an elastic modulus from about 15 GPa to about 22 GPa, the pyrocarbon coating has an average thickness ranging from about 100 to about 1000 microns.

8. The cartilage implant of claim 1, wherein the pyrocarbon coating has an elastic modulus of about 20 GPa and a strength of at least 400 MPa.

9. The cartilage implant of claim 8, wherein the upper face and oval perimeter of the articular end are polished, and the lower face and stem are coated with hydroxyapatite.

* * * * *